United States Patent [19]

Rottmaier et al.

[11] Patent Number: 4,658,026

[45] Date of Patent: Apr. 14, 1987

[54] N,N'-BIS(2,3-EPOXYPROPYL) DERIVATIVES OF CYCLIC DICARBOXYLIC ACID HYDRAZIDES AND A PROCESS FOR THE PRODUCTION THEREOF

[75] Inventors: Ludwig Rottmaier, Odenthal-Gloebusch; Rudolf Merten, Leverkusen, both of Fed. Rep. of Germany

[73] Assignee: Bayer Aktiengesellschaft, Leverkusen, Fed. Rep. of Germany

[21] Appl. No.: 636,280

[22] Filed: Jul. 31, 1984

[30] Foreign Application Priority Data

Aug. 12, 1983 [DE] Fed. Rep. of Germany ....... 3329192

[51] Int. Cl.$^4$ ................ C07D 405/14; C07D 491/18; D06M 13/38; C09J 3/00
[52] U.S. Cl. .................................. 544/238; 544/234; 544/237
[58] Field of Search ........................................ 544/238

[56] References Cited

U.S. PATENT DOCUMENTS 3,692,705 9/1972 Newey et al. .................. 260/2 ED

FOREIGN PATENT DOCUMENTS 2037943 2/1971 Fed. Rep. of Germany .
2263827 7/1973 Fed. Rep. of Germany .
2300010 7/1973 Fed. Rep. of Germany .
 150465 9/1981 German Democratic Rep. .

OTHER PUBLICATIONS

Fischer et al., Chem Abs 102, 6428s (1984).
Atassi et al., Chem Abs 102, 55644t (1984).
Dorn et al., Chem Abs 86, 171482p.
Chemical Abstracts, vol. 98, No. 11, Mar. 14, 1983, No. 98:89286s, p. 552.

*Primary Examiner*—Mark L. Berch
*Attorney, Agent, or Firm*—Connolly & Hutz

[57] ABSTRACT

The present invention relates to new N,N'-bis-(2,3-epoxypropyl) derivatives of cyclic dicarboxylic acid hydrazides and to a process for their production.

3 Claims, No Drawings

N,N'-BIS(2,3-EPOXYPROPYL) DERIVATIVES OF CYCLIC DICARBOXYLIC ACID HYDRAZIDES AND A PROCESS FOR THE PRODUCTION THEREOF

The present invention relates to new N,N'-bis-(2,3-epoxypropyl) derivatives of cyclic dicarboxylic acid hydrazides and to a process for their production.

The production of O-substituted monoglycidyl derivatives of maleic acid hydrazide is known from DD-PS No. 118641. According to claims 1 and 2 of this patent, maleic acid hydrazide may be converted into O-substituted O-monoepoxide in the presence of from 1.3 to 3 mols of alkali hydroxide (should n represent zero and $R^1$ and $R^4$ represent H in formula XIV of claim 1) despite the excess of from 2 to 5 mols of epichlorohydrin. New, paritially radically copolymerisable N,N'-bis-(2,3-epoxypropyl) derivatives of cyclic dicarboxylic acid hydrazides could surprisingly be produced if specific procedural conditions were observed.

The present invention thus provides N,N'-bis-(2,3-epoxypropyl) derivatives of cyclic dicarboxylic acid hydrazides corresponding to the general formula I:

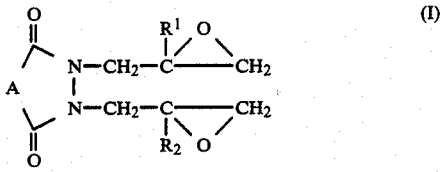

wherein
$R^1$ and $R^2$ are the same or different and each represents a hydrogen atom or a methyl group, preferably a hydrogen atom
A represents the radicals

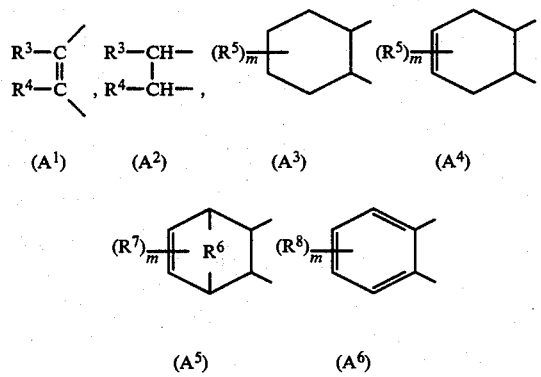

preferably ($A^1$), ($A^4$), ($A^5$) and ($A^6$),
$R^3$ and $R^4$ are the same or different and represent a hydrogen atom, a straight-chain or branched chain $C_1$–$C_4$ alkyl group, a halogen atom or a $C_1$–$C_4$-alkoxy group, preferably a hydrogen atom or a methyl group,
$R^5$ represents a straight-chain $C_1$–$C_4$-alkyl group or a halogen atom, preferably a methyl group or chlorine,
$R^6$ represents a $CH_2$-group, a $CCl_2$-group or an oxygen atom, preferably a —$CH_2$-group,
$R^7$ and $R^8$ represent a halogen atom, preferably chlorine and m represents 0 or an integer of from 1 to 4, and most preferably the number 0.

The following are particularly preferred: N,N'-bis-(2,3-epoxypropyl) derivatives of maleic acid-, citraconic acid-, tetrahydrophthalic acid-, phthalic acid- and endomethylene-tetrahydrophthalic acid hydrazide.

The N,N'-bis-(2,3-epoxypropyl) derivatives of the cyclic dicarboxylic acid hydrazides corresponding to the general formula (I) are obtained by reacting cyclic dicarboxylic acid hydrazides corresponding to the formula (II):

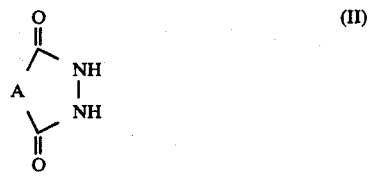

wherein A is as defined in formula (I), are reacted with excess epihalohydrin or β-methylhalohydrin, such as epichlorohydrin, epibromohydrin or β-methyl-epichlorohydrin in the presence of a suitable catalyst to produce the corresponding N,N'-bis-(halohydrins) of these hydrazides, and subsequently separating resulting by-products by drawing them off by suction and/or washing them out with water and splitting off hydrogen halide by treatment with hydrogen halide acceptors.

The hydrazides which are used to produce the new glycidyl compounds corresponding to the general formula (I) are for the most part known from the literature or may be produced according to known processes, such as from unsaturated anhydrides, acids, esters, and hydrazine, as is described in C.A. 78,147984 t or in the Journal of the American Chemical Society 80, 3790 (1958). The saturated hydrazides may be obtained from the corresponding unsaturated hydrazides, for example succinic acid hydrazide may be obtained from maleic acid hydrazide as described in the Journal of the American Chemical Society 73, 4716 (1951).

The following examples may be used: maleic acid hydrazide, citraconic acid hydrazide, succinic acid hydrazide, tetrahydrophthalic acid hydrazide, methyltetrahydrophthalic acid hydrazide, endomethylene tetrahydrophthalic acid hydrazide, methyl-endomethylene tetrahydrophthalic acid hydrazide, phthalyl hydrazide, tetrachlorophthalyl hydrazide and hexahydrophthalic acid hydrazide.

According to the present process, in the first stage a cyclic hydrazide is reacted with an epihalohydrin in the presence of a suitable catalyst to produce a halohydrin compound corresponding to the general formula (III):

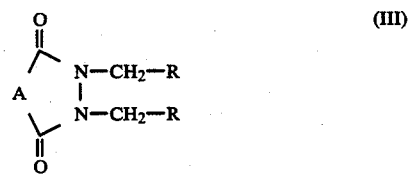

in which A represents the radicals as defined for formula (I) and the radicals R represent radicals which may be converted into 1,2-epoxyethyl radicals.

A radical R of this type which may be converted into a 1,2-epoxyethyl radical is, in particular, a hydroxy haloethyl radical which carries functional groups at various carbon atoms, such as 2-chloro-1-hydroxy- or 2-methyl-2-chloro-1-hydroxy ethyl radicals.

Quaternary ammonium salts such as trimethylbenzyl ammonium hydroxide, tetraethyl ammonium chloride, trimethyl benzyl ammonium chloride and trimethyl phenyl ammonium chloride are preferably used as catalysts in the addition of the halohydrin.

Furthermore, imidazolines, such as 2-phenyl imidazoline, 2-phenyl-4-methyl imidazoline, 2-methyl imidazoline, 2,4-dimethyl imidazoline, 2-benzylimidazoline, 1,2.phenylene-bis-imidazoline and tetramethylene-bisimidazoline are also suitable.

Another group of suitable catalyst are cyclic amidines corresponding to the general formula (IV)

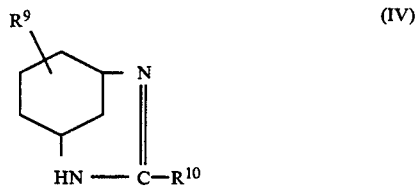

wherein
$R^9$ represents a hydrogen atom or an alkyl group having from 1 to 4 carbon atoms, and
$R^{10}$ represents a hydrogen atom or an organic radical, in particular methyl, ethyl, propyl, 2-ethylhexyl, stearyl, cyclohexyl, phenyl and benzyl.

The production of these cyclic amidines is described in German Offenlegungsschrift No. 30 41 834.

Tertiary amines such as triethylamine, tri-n-butylamine, triethanol amine, N,N'-dimethyl aniline, benzyl dimethyl amine, pyridine, endoethylene piperazine, N,N'-dimethyl piperazine, 4-dimethyl aminomethyl-2,6-di-tert.-butyl-phenol and 2,4,6-tris-dimethyl aminomethyl-phenol are also suitable.

The quantity of catalyst is preferably from 0.01 to 10 mol %, based on cyclic dicarboxylic acid hydrazide.

The cyclic carboxylic acid hydrazides are reacted with the epihalohydrin with at least equivalent quantities of epihalohydrin, that is one hydrazide group is reacted with at least two mols of epihalohydrin. However an excess of epihalohydrin, that is from 4 to 60 mols and most preferably from 10 to 30 mols of epihalohydrin are preferably used per hydrazide group. For economic reasons, the quantity of epihalohydrin is kept as low as possible.

The hydrazides and epihalohydrin may be reacted at from 20° to 160° C., preferably at from 30° to 80° C. and most preferably at from 40° to 60° C., optionally under increased pressure. If tertiary amines and in particular strong basic tertiary amines are used as the catalyst, 60° C. should not be exceeded since otherwise a particularly large amount of by-products will be formed which would substantially impair the formation of N,N'-diepoxides during dehydrohalogenation. This effect becomes more pronounced if the by-products are not removed before dehydrohalogenation.

The reaction times generally range from 30 minutes to several days, and in specific cases may be above or below these limits. If the reaction conditions, such as pressure, are appropriately selected, shorter reaction times may be achieved.

The by-products which are produced during the addition of the halohydrins to the hydrazides are removed from the reaction mixture before the second stage. The by-products may be removed by drawing off by suction the efflorescent impurities and/or by washing them out with water.

In a second stage, the halohydrin compound, first and foremost the bischlorohydrin hydrazide which may already contain certain quantitites of glycidyl compounds depending on the excess of epihalohydrin or β-methyl halohydrin, is subsequently dehydrohalogenated using hydrogen halide-splitting compounds to produce the N,N'-bis-(2,3-epoxypropyl) derivatives of the cyclic dicarboxylic acid hydrazides.

The compounds giving an alkaline reaction which are used for splitting the hydrogen halide are particularly alkali- or alkaline earth metal hydroxides such as sodium hydroxide, potassium hydroxide, calcium hydroxide, preferably sodium hydroxide. This may be used in solid form or in solution, and preferably in from 20 to 50% aqueous solutions.

Alkali carbonates, in particular soda and potassium carbonate in solid or dissolved form, alkali silicates, alkali phosphates and alkali aluminates and excess epihalohydrin or 1,2-alkylene oxides such as ethylene oxide may also be used for splitting the hydrogen halide, and if epichlorohydrin is used it is converted into glycerine dichlorohydrin.

From 1 to 1.2 equivalents of the hydrogen halidesplitting compounds are used for every halohydrin group of the compounds corresponding to formula (III).

It is effective in splitting the hydrogen halide, if the pH value does not exceed 13 and preferably does not exceed pH 11. To.this end, the alkali is gradually added, or the solution is gradually added dropwise while the pH value of the reaction mixture is monitored.

The hydrogen halide may be split at a temperature ranging from 20° C. to 120° C. If the hydrogen halide is split using alkali, such as aqueous potassium hydroxide, a reaction temperature of 70° C. should not be exceeded if optimum yields are to be obtained.

The best results are achieved at a temperature in the range of from 25° to 35° C. If alkali carbonates are used, the reaction temperature should be greater than 70° C. the upper limit generally being preset by the boiling temperature of the excess epihalohydrin.

It is advantageous to add a water-immiscible organic solvent during dehydrohalogenation, in order, azeotropically to remove the water which is produced during the reaction or is added dropwise via the alkali solution. The quantity of solvent which is added is not critical. Suitable solvents are chlorinated hydrocarbons such as methylene chloride, chloroform, ethylene chloride or trichloroethylene. If a great excess of epihalohydrin is used to produce the bis-(chlorohydrin) compounds of cyclic dicarboxylic acid hydrazides, the excess epihalohydrin may act as a water-immiscible solvent.

A particularly preferred embodiment consists of reacting in a first stage hydrazides corresponding to the formula (II) with epihalohydrin, preferably epichlorohydrin, in the presence of a suitable catalyst, and preferably a quaternary ammonium base, a quanternary ammonium salt, an imidazoline or a cyclic amidine, then removing resulting by-products by drawing them off by suction or washing them out with water and in a second stage treating the resulting hydrazide containing halohydrin groups with hydrogen halide-splitting compounds, and in particular alkali-, alkaline earth hydroxide, or alkali carbonates in solid or dissolved form.

The bis-(2,3-epoxypropyl) dicarboxylic acid hydrazides are generally worked up by removing by means of suction the by-product which is produced during the splitting of the halide, such as sodium chloride by using sodium hydroxide as acid trap. Sodium chloride and alkali residue which are still present are optionally removed by washing them out with water.

Of course the total quantity of sodium chloride and the alkali residue which is possibly still present may also be removed by washing them out with water without previously drawing them off by suction. The remaining solution is then optionally removed under vacuum optionally after drying using a suitable drying agent such as water-free sodium sulphate, from the solvent which may be excess epichlohydrin and which may be simultaneously reused in the next stages, and the resulting light-yellow to yellow viscous oils are crystallised by dissolving them in suitable solvents such as $C_1$–$C_4$-alkanols, preferably methanol, ethanol, ketones such as methyl ethyl ketone, glycol or diglycol monoethers or the acetates thereof such as ethylene-glycol-monomethyl-ether, diethylene-glycolmonomethyl-ether and ethylene-glycol-monoethyl-ether acetate, acetic acid esters such as acetic acid ethyl ester or butyl ester, aromatic hydrocarbons, such as toluene or xylene or the mixtures thereof, and subsequently cooling them.

The resulting crystalline compounds may be drawn off by suction and optionally further purified by recrystallisation, for example from ethanol or acetic acid butyl ester. It is often possible to avoid a purification stage and directly subject the raw product to processing.

Depending on the constitution of the radical A, viscous resins are frequently produced which may then be subsequently reacted without further purification.

The glycidyl-hydrazides which are obtained according to the present invention have epoxide values of from 0.3 to 0.893, preferably from 0.5 to 0.893. "Epoxide value" is to be understood as designating the total number of epoxide equivalents which are contained in 100 g of substance.

The epoxide equivalent is defined as beng the gram quantity of substance in which a 1,2-epoxide group is contained.

A 1,2-epoxide group is equivalent to one mol of hydrogen halide.

The polyglycidyl compounds which are produced according to the present invention may be used on their own or in combination with conventional hardeners, as impregnating agents for textiles such as fibres consisting of polyester, as coating agents, such as for painting onto glass, metals and wood, as adhesives for plastics of the most varied type, such as for sticking unwoven textile-like bodies and for producing mouldings, such as casting, pressing bodies and laminates.

The subsequent examples illustrate the present invention in more detail, and, unless otherwise specified the percentages mean percentages, by weight, and parts means parts, by weight.

EXAMPLE 1

112 g of maleic acid hydrazide, 1200 g of epichlorohydrin and 2 g of tetraethyl ammonium chloride are stirred for 20 hours at 60° C. After cooling, undissolved constituents are drawn off by suction and 180 g of a 45 % aqueous sodium hydroxide solution are added dropwise at 30° C. to an epichlorohydrin solution. The reaction is subsequently completed by stirring the solution for 4 hours at 30° C. The greasy sodium chloride which is produced may be washed out after addition of 250 g of water. The organic phase is once more washed with 100 g of water, dried using sodium sulphate and concentrated under vacuum at 50° C. and under 0.3 mbars. 124 g of a light-brown epoxide resin are obtained, which is thoroughly crystallised overnight and which, according to gas chromatographic analysis (=GC) substantially consists of N,N'-bis(2,3-epoxypropyl)-maleic acid hydrazide (degree of purity 93.8%). The pure N,N'-bis(2,3-epoxypropyl)maleic acid hydrazide having a melting point of 58° C. may be obtained from acetic acid butyl ester by recrystallisation, the structure of which may be confirmed using IR- and NMR spectra and elementary analysis.

Calculated for $C_{10}H_{12}N_2O_4$ (224.2): C 53.57%, H 5.40%, N 12.50% . Found: C 53.7%, H 5.5%, N 12.4%.

EXAMPLE 2

112 g of maleic acid hydrazide, 1200 g of epichlorohydrin and 2 g of the amidine corresponding to formula IV, in which $R^9$ represents methyl and $R^{10}$ represents phenyl, are stirred for 34 hours at 60° C. and subsequently worked as described in Example 1. 113 g of a brownish resin are obtained which according to GC substantially consists of N,N'-bis(2,3-epoxypropyl)-maleic acid hydrazide (degree of purity 94.1%).

EXAMPLE 3

112 g of maleic acid hydrazide, 1200 g of epichlorohydrin and 2 g of tetraethyl ammonium chloride are stirred for 3 hours at 80° C., the solution having to be cooled during this time due to the onset of the exothermic reaction. The solution which is still warm, is agitated with 200 g of water and mixed in portions at 30° C. with 80 g of solid sodium hydroxide. The reaction is completed by subsequently stirring the solution for 4 hours at 30° C. and drawing off by suction the resulting sodium chloride. After the epichlorohydrin solution has been washed out with 100 g of water, the solution is dried using $Na_2SO_4$, filtered and concentrated at 50° C./0.3 mbars. 107 g of a viscous oil is produced which gradually solidifies and which according to GC substantially consists of N,N'-bis-(2,3-epoxypropyl)-maleic acid hydrazide.

EXAMPLE 4

63 g of citraconic acid hydrazide, 800 g of epichlorohydrin and 1 g of tetraethyl ammonium chloride are stirred for 12 hours at 60° C. and agitated with 100 g of water. Then at a sump temperature of about 35° C., 100 g of a 40% aqueous sodium hydroxide solution are added dropwise under azeotropic reflux so that the water which is added dropwise and is produced during the reaction may be drawn off by suction. To complete the reaction, the solution is subsequently stirred for 2 hours under azeotropic reflux and the sodium chloride is drawn off by suction. The epichlorohydrin solution is twice agitated with 150 g of water, dried using sodium sulphate concentrated at 50° C./0.3 mbars. 138 g of a brownish, viscous oil is produced which has an epoxide value of 0.74 and a chlorine content of 1.2% which according to the NMR spectrum mainly consists of the N,N'-bis(2,3-epoxypropyl)citraconic acid hydrazide (GC:89.9%).

EXAMPLE 5

81 g of phthalic acid hydrazide, 1000 g of epichlorohydrin and 1 g of tetraethyl ammonium chloride are stirred for 4 hours at 80° C. and are drawn off by suction after cooling. The epichlorohydrin solution is mixed with 100 g of a 40% aqueous sodium hydroxide solution at 30° C., stirred for 4 hours at 30° C. and then washed out with 300 g of water and finely with 100 g of water. After drying of the organic phases and concentration at 60° C. and under 0.3 mbars, 83 g of a viscous, yellowish resin are produced which have an epoxide value of 0.59 and a chlorine content of 2.3%, from which the pure N,N'-diglycidyl phthalic acid hydrazide having a melting point of 102° C. is obtained by crystallisation with an ethanol/isopropanol mixture. IR- and NMR spectra and elementary analysis confirm the assumed structure. Calculated for $C_{14}H_{14}N_2O_4$ (274.3): C 61.30%, H 5.14%, N 10.21%. Found: C 61.2%, H 5.2%, N 10.3%.

EXAMPLE 6

112 g of maleic acid anhydride, 1200 g of epichlorohydrin and 10 g of tetraethyl ammonium chloride are stirred for 20 hours at 40° C. and subsequently processed as described in Example 1. 109 g of a yellow resin are obtained which according to GC analysis substantially consist of N,N'-bis-(2,3-epoxypropyl)-maleic acid hydrazide (degree of purity 92.9%).

EXAMPLE 7

112 g of maleic acid hydrazide, 1200 g of epichlorohydrin and 1.5 g of triethylamine are stirred for 16 hours at 60° C. Insoluble constituents are removed by suction. After dehydrohalogenation with 180 g of 45% aqueous sodium hydroxide solution, the solution is worked up as described in Example 1. 119 g of a brownish epoxide resin are obtained which according to GC analysis consists of N,N'-bis-(2,3-epoxypropyl)-maleic acid hydrazide and has a degree of purity of 95.8%.

EXAMPLE 8

41.5 g of tetrahydrophthalic acid hydrazide, 500 g of epichlorohydrin and 0.5 g of tetraethyl ammonium chloride are stirred for 25 hours at 80° C. and after cooling are washed out with 100 g of water. 50 g of a 40% aqueous sodium hydroxide solution are added dropwise to the epichlorohydrin solution at 30° C. and to complete the reaction the solution is subsequently stirred for 7 hours at 30° C. The sodium chloride is removed by twice washing it out with 200 g of water. After drying using sodium sulphate and concentration at 60° C. and under 0.3 mbars, 36.5 g of a light-yellow, viscous epoxide resin having an epoxide value of 0.62 and a chlorine content of 2.1 are obtained which substantially consists of N,N'-bis-(2,3-epoxypropyl)tetrahydrophthalic acid hydrazide.

PRACTICAL EXAMPLE 100 g of N,N'-diglycidyl phthalic acid hydrazide and 112 g of hexahydrophthalic acid anhydride are separately melted down, mixed at 110° C. and cast in a mould. After hardening over a period of 4 hours at 80° C. and over a period of 16 hours at 160° C. sample bodies are produced which have the following mechanical properties: Flectional resistance according to DIN 53452 in $N/mm^2$ 158 Permanent deformation according to DIN 53452 in $N/mm^2$ 3.8 Impact strength according to DIN 53453 in $KJ/m^2$ 9.5 Indentation hardness according to DIN 53456 in $N/mm^2$ 180 Martens degree according to DIN 53458 in °C. 167.

COMPARATIVE EXAMPLE 1

This Example shows that if the by-products which are produced during the reaction of the hydrazides with epihalohydrin in the presence of tertiary amines are not separated, a reaction product containing an expoxide group is obtained after dehydrohalogenation, which contains only very small quantities of N,N'-bis-(2,3-epoxypropyl)-dicarboxylic acid hydrazide.

112 g of maleic acid hydrazide, 1200 g of epichlorohydrin and 1.5 g of triethylamine are stirred for 16 hours at 60° C. After cooling and without the byproducts being separated the process is immediately continued as described in Example 7 with addition of 180 g of 45% aqueous sodium hydroxide solution. 117 g of a brownish epoxide resin having an epoxide value of 0.65 are obtained, which does not crystallize even after being stored for 4 weeks. According to GC analysis, the resin contains 27.1% of N,N'-bis-(2,3-epoxypropyl)maleic acid hydrazide.

COMPARATIVE EXAMPLE 2

This comparison shows that at a temperature of more than 60° C. and if tertiary amines are used as catalysts and if the by-products are not separated after the reaction of the hydrazides with epihalohydrin, the yields of N,N'-diepoxides are further reduced.

112 g of maleic acid hydrazide, 1200 g of epichlorohydrin and 1.5 g of triethylamine are stirred for 45 minutes at reflux temperature. After cooling the process is continued as described in Example 7 with 180 g of 45% aqueous sodium hydroxide solution. 109 g of a black/brown, noncrystallising resin are obtained which according to GC analyses contains 19.2% of N,N'-bis-(2,3-epoxypropyl)maleic acid hydrazide.

COMPARATIVE EXAMPLE 3

This experiment shows that if the carboxylic acid hydrazides are directly reacted with epihalohydrin in the presence of strong bases, no N,N'-bis-(2,3-epoxypropyl)dicarboxylic acid hydrazide is obtained.

As described in Example 1 of DD-PS No. 118641, 22.4 g of maleic acid hydrazide (0.2 mols), 22.4 g of potassium hydroxide, 20 g of water, 74 g (0.8 mols) of epichlorohydrin (corresponding to 2 mols per NH group) and 250 ml of ethanol are stirred for 4 hours at 70° C. until maleic acid hydrazide can no longer be detected. The resulting precipitate of potassium chloride is drawn off by suction and the filtrate is concentrated under reduced pressure (about 20 mbars) at 40° C. over a period of 4 hours. 46.5 g (a theoretical yield of 44.8) of a light-yellow, viscous oil are obtained which does not crystallize even after being left to stand for 4 weeks (even after stirring with solvents such as methanol, acetone, acetic acid ethyl ester and acetic acid butyl ester). The epoxide value of the resulting oil directly after production is 0.33 (theoretical epoxide value for a diepoxide is 0.89).

By means of thin-layer chromatographic analysis (eluant 80% by volume of chloroform and 20% by volume of methanol), N,N'-(bis-(2,3-epoxypropyl)-maleic acid hydrazide can no longer be detected.

We claim:
1. N,N'-bis(2,3-epoxypropyl) derivatives of cyclic dicarboxylic acid hydrazides corresponding to the formula (I):

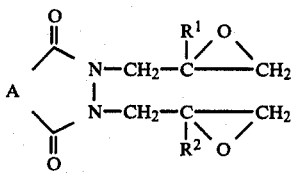

wherein

R$^1$ and R$^2$, which may be the same or different, each represents a hydrogen atom or a methyl group, A represents the radicals

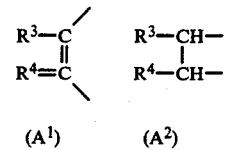

where R$^3$ and R$^4$, which are the same or different, represent a hydrogen atom or a straight-chain or branched chain C$_1$–C$_4$ alkyl group, a halogen atom, or a C$_1$–C$_4$-alkoxy group.

2. N,N'-bis-(2,3-epoxypropyl) derivatives of cyclic dicarboxylic acid hydrazides according to claim 1, wherein in formula (I)

R$^1$ and R$^2$ each represents a hydrogen atom,

A represents the radical (A$^1$),

R$^3$ and R$^4$, which may be the same or different, each represents a hydrogen atom or a methyl group.

3. N,N'-bis-(2,3-epoxypropyl) derivatives according to claim 1 which are derivatives of maleic acid- and citraconic acid- hydrazide.

* * * * *